(12) United States Patent
Strickland et al.

(10) Patent No.: US 7,047,974 B2
(45) Date of Patent: May 23, 2006

(54) NASAL CANNULA

(75) Inventors: Roger Strickland, Waycross, GA (US); Jonathan Lee, St. Augustine, FL (US)

(73) Assignee: InnoMed Technologies, Inc., Coconut Creek, FL (US)

( * ) Notice: Subject to any disclaimer, the term of this patent is extended or adjusted under 35 U.S.C. 154(b) by 0 days.

(21) Appl. No.: 10/689,174

(22) Filed: Oct. 20, 2003

(65) Prior Publication Data

US 2004/0134498 A1    Jul. 15, 2004

Related U.S. Application Data

(62) Division of application No. 10/042,042, filed on Oct. 25, 2001, now Pat. No. 6,679,265.

(51) Int. Cl.
*A61M 15/08* (2006.01)

(52) U.S. Cl. .................... 128/207.18; 128/206.11

(58) Field of Classification Search .......... 128/204.24, 128/202.18, 203.22, 203.29, 204.12, 205.25, 128/206.11, 206.12, 206.18, 206.21, 206.27, 128/206.28, 207.11, 207.14, 207.18; 600/529, 600/532, 538
See application file for complete search history.

(56) References Cited

U.S. PATENT DOCUMENTS

| | | | |
|---|---|---|---|
| 1,125,542 A | 1/1915 | Humphries | |
| 3,670,726 A | 6/1972 | Mahon et al. | |
| 3,739,774 A | 6/1973 | Gregory | |
| 3,861,385 A | 1/1975 | Carden | |
| 3,902,486 A | 9/1975 | Guichard | |
| 3,905,361 A | 9/1975 | Hewson et al. | |
| 4,151,843 A * | 5/1979 | Brekke et al. | 128/205.25 |
| 4,156,426 A | 5/1979 | Gold | |
| 4,267,845 A | 5/1981 | Robertson, Jr. et al. | |
| 4,273,124 A | 6/1981 | Zimmerman | |
| 4,312,359 A | 1/1982 | Olson | |
| 4,367,735 A | 1/1983 | Dali | |
| 4,367,816 A | 1/1983 | Wilkes | |
| 4,406,283 A | 9/1983 | Bir | |
| 4,422,456 A | 12/1983 | Teip | |
| 4,493,614 A | 1/1985 | Chu et al. | |
| 4,549,542 A | 10/1985 | Chien | |
| 4,587,967 A | 5/1986 | Chu et al. | |
| 4,601,465 A | 7/1986 | Roy | |
| 4,617,637 A | 10/1986 | Chu et al. | |
| 4,660,555 A | 4/1987 | Payton | |
| 4,699,139 A | 10/1987 | Marshall et al. | |
| 4,706,664 A | 11/1987 | Snook et al. | |

(Continued)

FOREIGN PATENT DOCUMENTS

DE    146688    2/1981

(Continued)

OTHER PUBLICATIONS

Snapp Nasal Interface, Tiara Medical Systems, Inc. http://www.tiaramed.com/asp_shop/shopdisplayproducts.asp?id=109&cat=SNAPP%2A+Nasal+Interface, viewed May 17, 2005.

*Primary Examiner*—Teena Mitchell
(74) *Attorney, Agent, or Firm*—Olds, Maier & Richardson PLLC

(57) ABSTRACT

A nasal cannula for delivering air to a patient's nares. Two delivery tubes are provided to supply air to a pair of nasal inserts each of which conform to the shape of the nare. Properly placed bleed ports reduce noise and reduce carbon dioxide retained in the system. The cannula is positioned on the face with the aid of a strap system.

20 Claims, 5 Drawing Sheets

U.S. PATENT DOCUMENTS

| | | | |
|---|---|---|---|
| 4,753,233 A | 6/1988 | Grimes | |
| 4,774,946 A | 10/1988 | Ackerman et al. | |
| 4,899,740 A | 2/1990 | Napolitano | |
| 4,915,105 A * | 4/1990 | Lee | 128/205.27 |
| 4,919,128 A * | 4/1990 | Kopala et al. | 128/207.18 |
| 4,996,983 A | 3/1991 | AmRhein | |
| 5,000,173 A | 3/1991 | Zalkin et al. | |
| 5,022,900 A | 6/1991 | Bar-Yona et al. | |
| 5,025,805 A | 6/1991 | Nutter | |
| 5,038,772 A | 8/1991 | Kolbe et al. | |
| 5,046,491 A | 9/1991 | Derrick | |
| 5,074,297 A | 12/1991 | Venegas | |
| 5,113,857 A | 5/1992 | Dickerman et al. | |
| 5,121,745 A | 6/1992 | Isreal | |
| 5,127,397 A | 7/1992 | Kohnke | |
| 5,137,017 A | 8/1992 | Salter | |
| D333,015 S | 2/1993 | Farmer et al. | |
| 5,188,101 A | 2/1993 | Tumolo | |
| 5,265,592 A | 11/1993 | Beaussant | |
| 5,265,595 A | 11/1993 | Rudolph | |
| 5,269,296 A * | 12/1993 | Landis | 128/207.18 |
| 5,271,391 A | 12/1993 | Graves | |
| 5,299,599 A | 4/1994 | Farmer et al. | |
| 5,335,656 A | 8/1994 | Bowe et al. | |
| 5,355,893 A | 10/1994 | Mick et al. | |
| 5,372,130 A | 12/1994 | Stern et al. | |
| 5,375,593 A | 12/1994 | Press | |
| 5,376,593 A | 12/1994 | Press | |
| 5,385,141 A | 1/1995 | Granatiero | |
| 5,394,568 A | 3/1995 | Brostrom et al. | |
| 5,396,885 A | 3/1995 | Nelson | |
| 5,398,676 A | 3/1995 | Press et al. | |
| 5,400,776 A | 3/1995 | Bartholomew | |
| 5,425,359 A | 6/1995 | Liou | |
| 5,437,267 A | 8/1995 | Weinstein et al. | |
| 5,477,852 A * | 12/1995 | Landis et al. | 128/207.18 |
| 5,509,409 A | 4/1996 | Weatherholt | |
| 5,526,806 A | 6/1996 | Sansoni | |
| 5,533,506 A | 7/1996 | Wood | |
| 5,682,881 A | 11/1997 | Winthrop et al. | |
| 5,687,715 A | 11/1997 | Landis et al. | |
| 5,724,965 A | 3/1998 | Handke et al. | |
| 5,740,799 A | 4/1998 | Nielson | |
| 5,794,619 A | 8/1998 | Edelman et al. | |
| 5,906,203 A | 5/1999 | Klockseth et al. | |
| 5,954,049 A | 9/1999 | Foley et al. | |
| 5,975,077 A * | 11/1999 | Hofstetter et al. | 128/204.24 |
| 6,478,026 B1 * | 11/2002 | Wood | 128/207.18 |
| 6,561,188 B1 | 5/2003 | Ellis | |
| 6,561,193 B1 * | 5/2003 | Noble | 128/207.18 |
| 6,571,798 B1 | 6/2003 | Thornton | |
| 6,595,215 B1 | 7/2003 | Wood | |
| 6,637,434 B1 | 10/2003 | Noble | |
| 6,655,385 B1 | 12/2003 | Curti et al. | |
| 6,679,265 B1 * | 1/2004 | Strickland et al. | 128/207.18 |
| 6,768,800 B1 | 7/2004 | Enamito et al. | |
| 6,807,967 B1 * | 10/2004 | Wood | 128/207.18 |
| 2002/0046755 A1 | 4/2002 | DeVoss | |
| 2002/0124849 A1 | 9/2002 | Billette de Villemeur | |
| 2005/0028822 A1 | 2/2005 | Sleeper et al. | |
| 2005/0033247 A1 | 2/2005 | Thompson | |
| 2005/0051178 A1 | 3/2005 | Riggins | |
| 2005/0061326 A1 | 3/2005 | Payne, Jr. | |

FOREIGN PATENT DOCUMENTS

| | | |
|---|---|---|
| EP | 93309991.3 | 6/1995 |
| GB | 0532214 | 1/1941 |
| WO | WO 01/97892 A1 | 6/2000 |

* cited by examiner

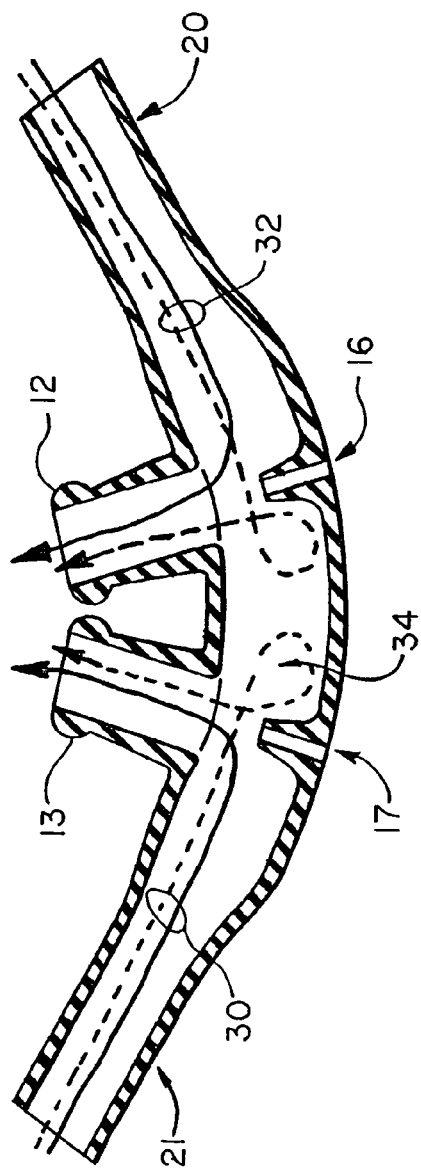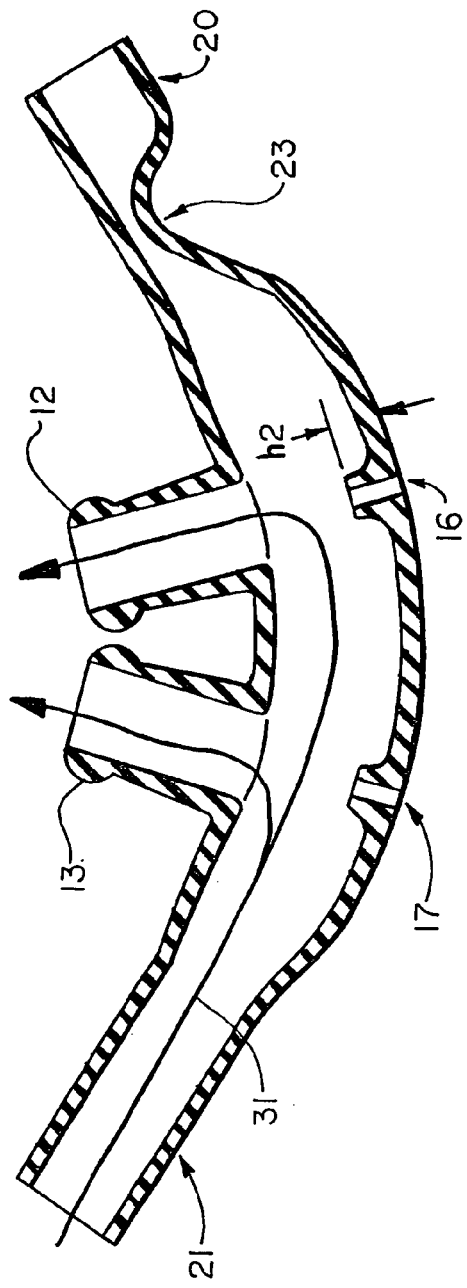

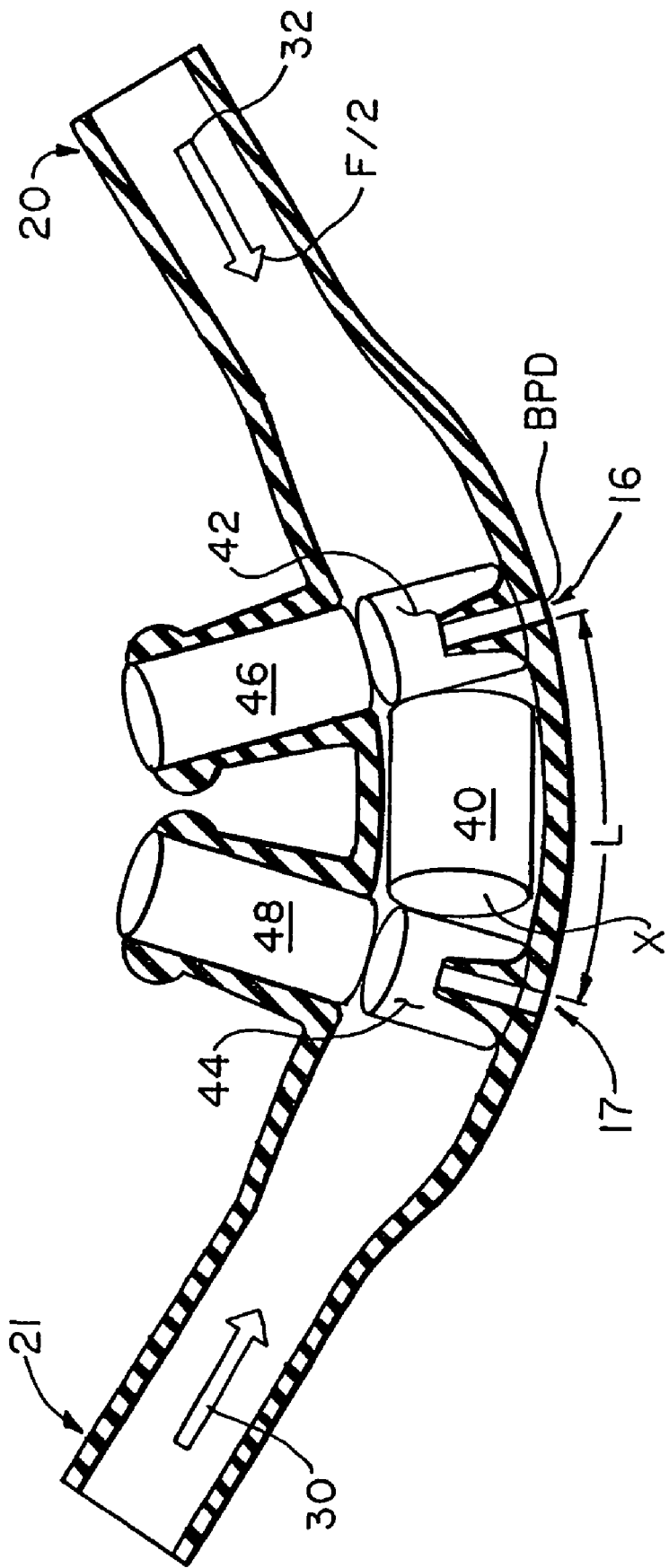

NASAL CANNULA

This is a division of Ser. No. 10/042,02, filed Oct. 25, 2001 now U.S. Pat. No. 6,679,265.

FIELD OF THE INVENTION

The present invention relates generally to a nasal mask or cannula and more particularly to a nasal cannula for treating a patient with a positive ventilation pressure machine for assisted ventilation.

BACKGROUND OF THE INVENTION

Positive air pressure (PAP) assisted ventilation systems have been adopted for the treatment of various disorders. PAP systems are commonly used to treatment sleep apnea. Variations of PAP systems have been used to administer drugs and the like.

In operation the patient's respiration is assisted by an external pump which supplies air to the patient under a slight positive pressure. In the conventional system, air is delivered in response to preset conditions selected for each individual patient. In normal operation the patient's inspiratory phase is assisted by a pump which delivers an adequate supply of air at a slight positive pressure to a mask or cannula that is placed on the face of the patient. Full face mask systems which cover both the mouth and the nose are used. Systems which cover the mouth or nose alone are also common.

In use, when the patient exhales, the higher pressure in the mask or cannula system is used to open an exhaust valve. Thus the patient respiration is assisted on the inhalation phase by positive pressure while the expiration phase takes place at approximately atmospheric pressure.

In instances where the patient compliance is affected by the comfort of the mask it is now widely accepted that "nose only" cannula devices are preferred. Examples of current devices can be seen in U.S. Pat. No. 5,477,852 to Landis; U.S. Pat. No. 5,533,506 to Wood; U.S. Pat. No. 5,269,296 to Landis; U.S. Pat. No. 5,687,715 to Landis; U.S. Pat. No. 5,724,965 to Handke.

SUMMARY OF THE INVENTION

In contrast to prior air nasal masks, the present system includes a pair of nasal inserts which are fed bilaterally from a pair of delivery tubes which includes both a left and a right leg. If the patient occludes one leg on one side of the mask, the complimentary side is sufficient to provide all of the air required by the patient.

Air is introduced into the system through a Y-shaped adapter or coupler. The shape of the coupler cooperates with other elements to minimize noise.

A pair of bleed ports are placed in the cannula body near the patient's nose. These bleed ports reduce the amount of carbon dioxide retained by the system. The two complex ports are placed in the cannula body to reduce noise and to reduce carbon dioxide build up in the system. Example calculations show how the size, shape and location of each of these ports cooperate to reduce the inhaled carbon dioxide concentration.

An additional feature relates directly to the shape of the nasal inserts. The nasal inserts are sufficiently long and compliant that they may be inserted into the nose until they adopt a location where the cross-section of the nare and the cross-section of the insert are essentially equal. The compliance of the material used to manufacturer the device is sufficient to provide an extremely comfortable fit in the nares.

BRIEF DESCRIPTION OF THE DRAWING

Throughout the figures of the drawing like reference numerals indicate identical structure wherein:

FIG. 3 is cross section of a portion of the nasal cannula showing the bleed ports;

FIG. 4 is cross section of a portion of the nasal cannula showing the bleed ports;

DETAILED DESCRIPTION

Figure 1:
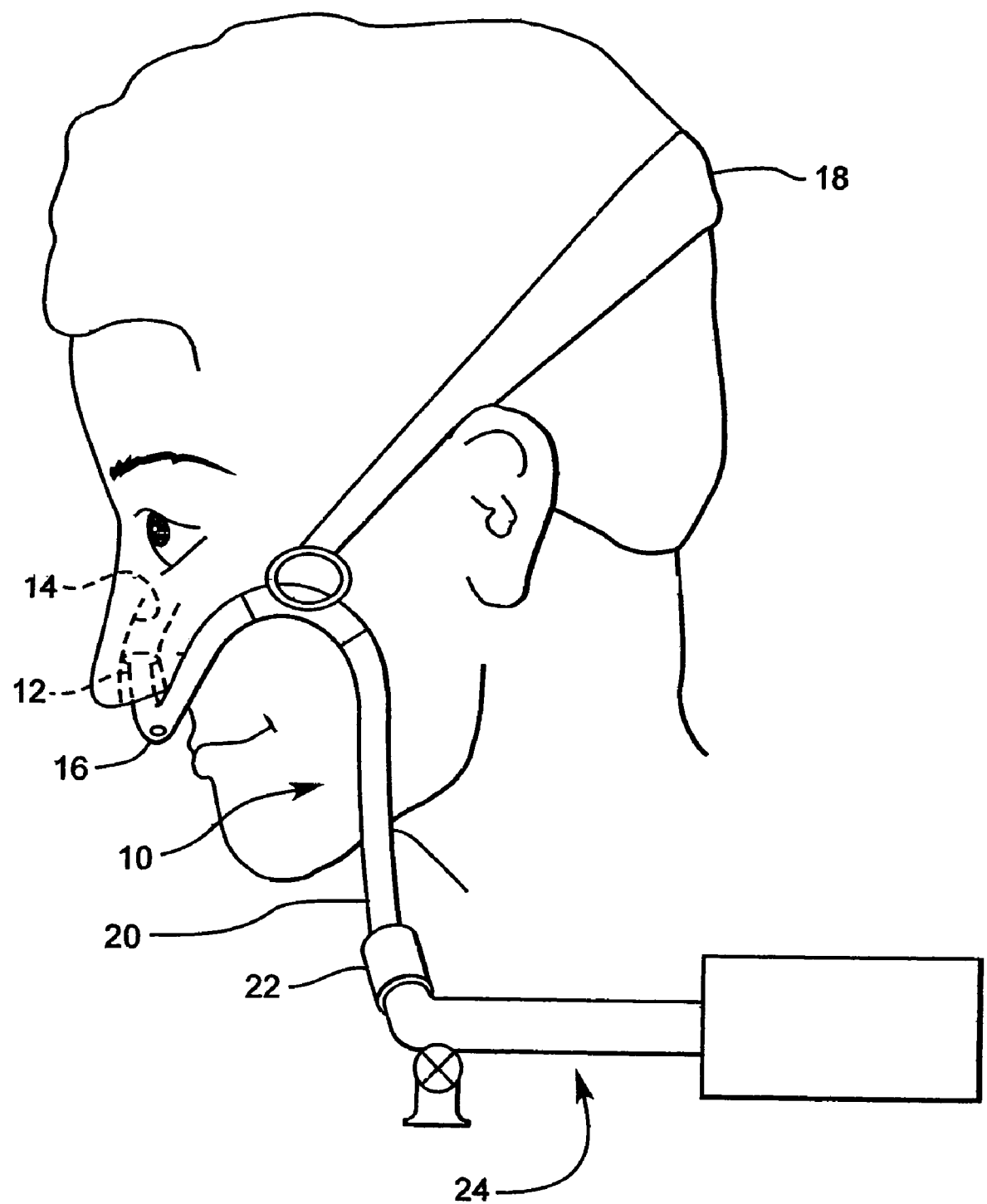
FIG. 1 is a schematic representation of the nasal cannula on the head of a user.

Turning to FIG. 1 there is shown a nasal cannula 10 which shows a nasal insert 12 placed into a patient's nare 14. Directly beneath each nasal insert is a bleed port as seen at reference numeral 16. The complete nasal cannula is held on the patient's face with a strap system 18 which may be of any convenient and conventional construction. The left and right delivery tubes typified by delivery tube 20 terminate in a coupler 22. This Y-shaped coupler 22 is connected to a conventional positive pressure ventilation machine 24.

In operation, the positive pressure ventilation machine 24 supplies air under pressure to the nasal cannula 10 and releases exhaled air to the atmosphere. Conventional machines have a valve that is overpressure during exhalation to exhaust air. In some instances the system may also warm and humidify the delivered air. In some instances the machines are used to deliver medications.

The left delivery tube and the right delivery tube 20 should lie close to the face of the patient and the coupler 22 should be positioned in the vicinity of the neck as seen in the figure.

Figure 2:
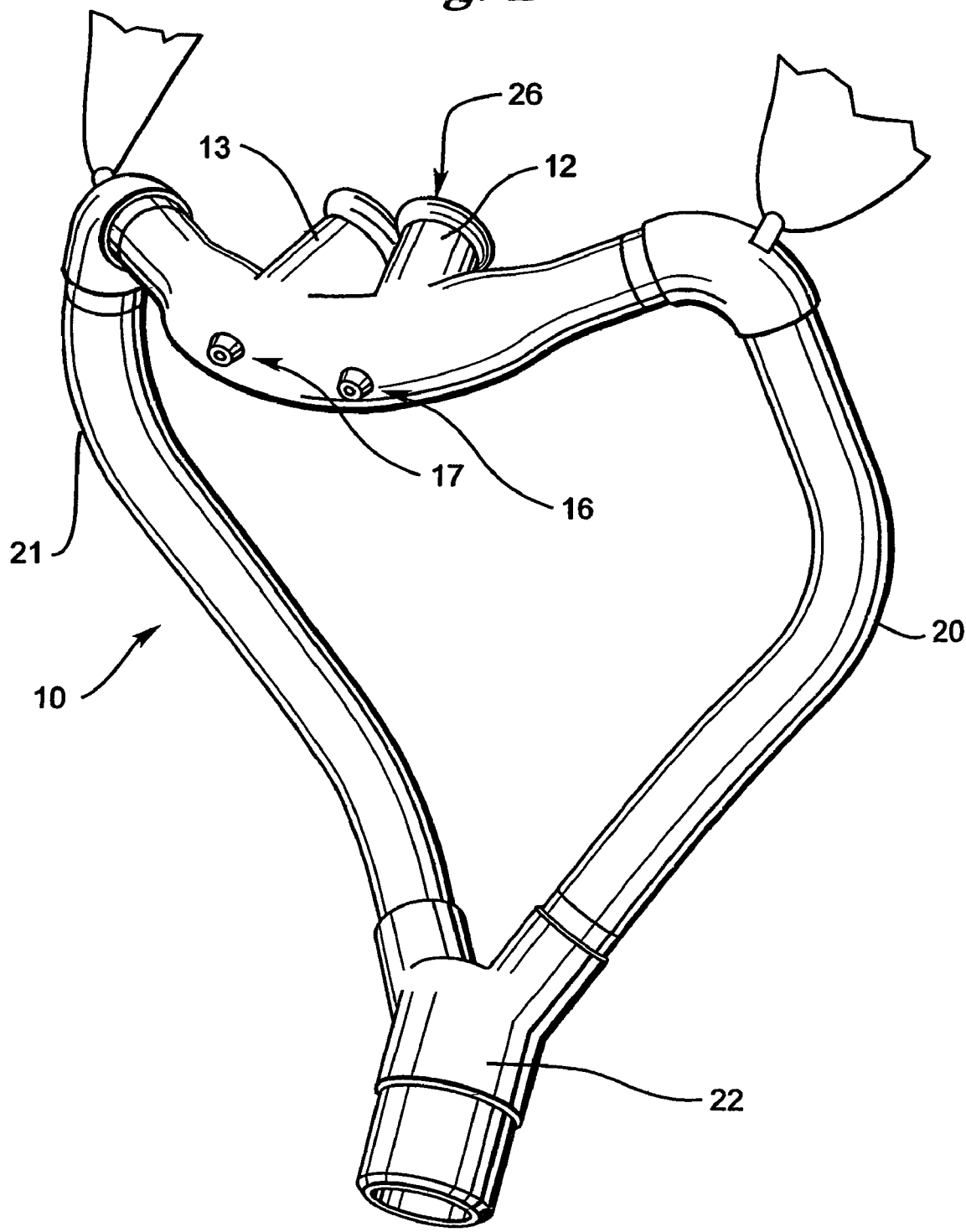
FIG. 2 is a projection of the nasal cannula in isolation.

FIG. 2 shows the nasal cannula 10 in perspective view. The entire cannula 10 may be molded out of a polymeric material such as silicone rubber or urethane. Portions of the nasal cannula may be locally reinforced to increase rigidity. For example it may be useful to reinforce the structure at the location where the strap 18 system meets the cannula device 10 In the figure a portion of the strap system 18 is shown coupled to delivery tube 20. The various changes in section depicted in the figure add stiffness or rigidity to the device. The optimal shape and cross section is not known and some experimentation may be required to optimize the device. However the softness and compliance of the elastomer is an important factor in patient comfort. The y-shaped connector 22 is adapted for connection to the PAP system 24.

Nasal insert 12 and nasal insert 13 are tubes connected to and extending from the delivery tube 20 and delivery tube 21 respectively. The most distal portion of the insert 12 terminates in a flange 26. It is expected that each flange 26 will be quite soft. The flange 26 is designed to readily conform to the patient's nare. In use the patient will direct the inserts into the nose and the inserts 12 and 13 will move in the nare until the cross section of the nare matches the cross section of the flange. The anatomy of the nose will deform the shape of the insert and its flange to achieve a comfortable seal. It is expected that only one or two sizes will be required to fit a large population as most patients have similarly sized nares.

The bleed port typified by port 16 is a tube extending from the delivery tube 20 into the insert 12. Each tube has a characteristic height or length. These bleed ports serve several functions. If the bleed ports 16 and 17 are appropriately placed and sized they can reduce the accumulation of carbon dioxide. If they are properly configured, sized and located they can also be used to decrease "whistling" or other acoustic effects. One objective of the bleed ports is to decreases the amount of carbon dioxide in the cannula during inhalation to a targeted value between 0.2 to 0.7 percent. A preferred value is below approximately 0.5 percent. Applicant believes that low carbon dioxide concentrations in the system will prevent build up of carbon dioxide in the patient.

FIG. 3 is a composite and schematic view that shows the air flow in the nasal cannula 10 during normal inhalation. Inspired air seen as arrows 30 and 32 depict flow under pressure from the air source 24. A small flow depicted by vortex 34 enters the space between insert 12 and insert 13. In normal operation each side of the system carries one half of the required flow.

FIG. 4 is a composite and schematic view that depicts an occlusion 23 or pinch off in the delivery tube 20. In use, when one of the delivery tubes such as delivery tube 20 is closed off by patient movement or the like, there is still sufficient air supplied through the alternate delivery tube 21 as indicated by the airflow 31 depicted in the figure. In this instance the full amount of air enters the patient through inserts 12 and 13 of the system. In the figure the height or length of the bleed port is shown as "h2" and this represents a minimum height bleed port 16. It is expected that the minimum height is twice the delivery tube thickness at the location of the bleed port.

Figure 5:
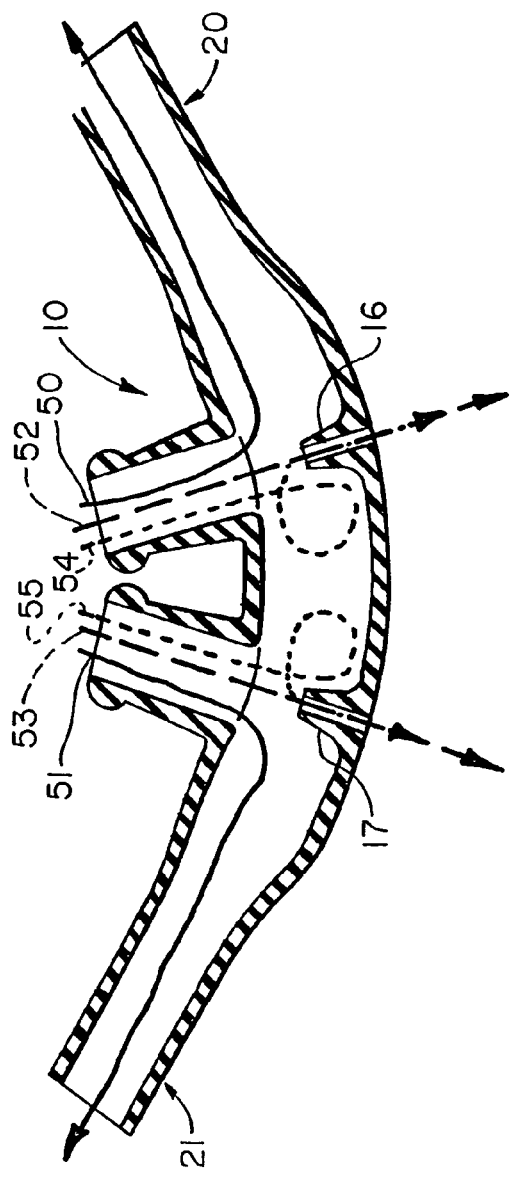
FIG. 5 is cross section of a portion of the nasal cannula showing the bleed ports.

FIG. 5 is a composite and schematic view that shows the idealized airflow in the nasal cannula 10. There are three distinct exit paths. Path 50 and path 51 depict flow back to the exhaust valve of the ventilator 24. This flow overpowers the exhaust valve and most of this flow leaves the system. Path 52 and 53 show exhaust directly through the bleed ports 16 and 17 respectively. The paths identified by path arrows 54 and 55 reflect complex scavenging of the volume between the inserts. This flow dilutes the air in the volume and helps to reduce carbon dioxide.

Figure 6:
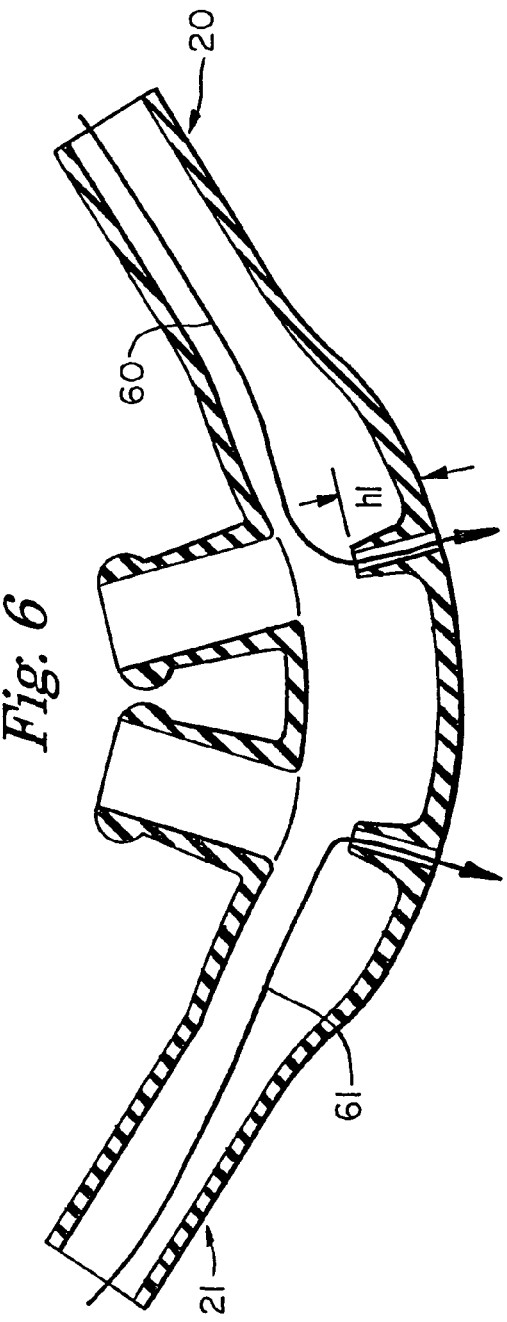
FIG. 6 is cross section of a portion of the nasal cannula showing the bleed ports; and, FIG. 7 is diagram of volumes and dimensions related to the calculation of the size and location of the bleed ports.

FIG. 6 is a composite and schematic view that shows airflow during the respiratory pause. In this phase the patient is neither inhaling or exhaling. During this portion of operation the air from the PAP ventilator 24 exits though bleed ports 16 and 17 as indicated by path arrows 60 and 61. In this figure "tall" bleed ports are depicted. The height value h1 is less than about 10 times the wall thickness at the location of the bleed port. The diameter of the bleed ports (BPD) is established to reduce the accumulation of carbon dioxide. The height of the bleed ports "h1 or h2" is established to reduce the incidence of parasitic acoustic effects. The relationship between the bleed port diameter (BPD) and the height (h1) is optimized between a value of 0.1 and 0.5. that is when 0.1=<(BPD/h1)=<0.5.

EXAMPLE

It is now recognized that simple ventilation systems which retain a large volume of exhaled gas within the air inlet track result in increased carbon dioxide concentration in the patient's blood. An increase in dissolved carbon dioxide results in the acidification of the blood and increases respiration drive and usually increases respiration rate. In the system the dead space of the device is balanced with both the size and location of the bleed port structures to prevent build-up of the concentration of carbon dioxide in the inhaled air. When the size and location of the ports is optimized, a significant reduction in carbon dioxide gas concentration is achieved.

Generally speaking if the bleed ports are to be small, they need to be located near the nasal inserts. This effect is more important if the dead space within the cannula is large. For this reason, it should be recognized that there is a relationship between dead space, bleed port location and size which can cooperate together to provide a nasal cannula with superior performance. Although it appears that the optimized ports are restrictive due to their length and size, it has also been determined that they can be shaped to minimize parasitic acoustic effects such as "whistling" which is exhibited by current generations of current nasal cannula.

Turning to FIG. 7 the dead space is the sum of all the cylinders shown in the figure as cylinders 40; 42;44; 46; and 48. The dead space is used in calculations to determine a suitable bleed port size (BPD). The immediate dead space volume is defined as the volume of the nasal inserts and the delivery tube between the inserts Simple geometry can be used to estimate the volume of the space through the cylinders depicted in FIG. 7. As the bleed ports 16 and 17 move laterally along the delivery tubes the volume of cylinder 40 increases by the distance between the inserts. Thus for the bleed port to pass the volume of the immediate dead space into the atmosphere within one second requires a computed area (BPD) related to the square root of the sum of the distance between the bleed ports. Thus for a given expiration time taken as one second and a desired concentration of carbon dioxide taken at 0.5 percent one can compute the size of the bleed port or any given distance or for any given bleed port the optimal distance between them. Based on these criteria the bleed port's diameter is related to the square root of the cross sectional area (X), the Immediate Deadspace (IDS) and the maximum system flow rate (F) as follows:

$$(\text{BPD}) \text{ Bleed Port Diameter} = 2\sqrt{\frac{X * IDS}{\pi * F}}$$

A first level approximation identifies that for a given bleed port of area (BPD), the separation distance of the bleed ports is inversely related to the square of the cannula cross sectional area (X)(see FIG. 7) and directly related to the maximum system flow rate (F) as follows:

$$\text{Bleed port separation distance} \cup \frac{A * F}{X^2}$$

It should be noted that if the ports are very far apart they need to be large to reach the carbon dioxide reduction goal, but such large bleed ports reduce the pressure in the system by such a large margin that it no longer effectively provides the positive pressure assistance.

Representative prototype devices have been fabricated with a diameter (X) of between 3/8 and 5/8 inches and other dimensions may be approximately scaled from FIG. 2.

Various modification and additions to the invention may be made without departing from the scope of the invention.

What is claimed:
1. A nasal cannula comprising:
first and second nasal inserts positioned on the nasal cannula with no indentation between the first and second nasal inserts for insertion into a patient's nares;
whereby the area of each insert and the area of the nare are essentially equal so that a positive air pressure seal is created between the nare and the insert;

a first delivery tube and a second delivery tube, each coupled to both of said nasal inserts, whereby each nasal insert communicates with both the first delivery tube and second delivery tube;

a coupler located remote from said nasal inserts for coupling said cannula to said source of respiration gas; and at least one bleed port positioned proximate a nasal insert communicating with said delivery tubes, having an opening flush with the exterior of the nasal cannula that is directly open to atmospheric pressure and having an internal height less than ten times the thickness of the delivery tube at the location of the bleed port.

2. The nasal cannula of claim 1 further comprising:

at least two tubular bleed ports each having an internal lumen;

each of said tubular bleed ports located directly in line with one of said nasal insert for preferentially intercepting expired gas during an exhalation, said bleed port having an characteristic bleed port diameter called BPD, and said bleed port separated by a distance called L.

3. The nasal cannula of claim 1 wherein:

said tubular bleed ports are located and sized to reduce the carbon dioxide content of inspired air to a value below approximately 0.5% carbon dioxide for the air inhaled from and retained by the delivery tubes.

4. The nasal cannula of claim 1 wherein:

said nasal inserts terminate in a compliant flange at their distal ends to conform to the nare of a patient.

5. The nasal cannula of claim 4 wherein:

each of said first or second nasal inserts has a characteristic length;

the length of either the first or second nasal insert are sufficiently long to allow an insert to move in the nasal passage until the cross section area of the nare and the cross section area of said nasal insert, are substantially the same, thereby forming a positive pressure seal between said nasal insert and said nare.

6. A nasal comprising:

two nasal inserts positioned on the nasal cannula with no indentation between the first and second nasal inserts for insertion into a patient's nares, each insert having a flange member at is terminal end for sealing against said nare against the positive air pressures;

a first delivery tube and a second delivery tube meeting together proximate the nares forming plenum, having a plenum volume; and one or more bleed ports directly inline with said nasal insert and having an opening flush with the exterior of the nasal cannula and an internal lumen having a height less than ten times the thickness of the delivery tube at the location of the bleed port providing unrestricted gas exchange with the environment; each bleed port having a characteristic diameter, selected depending on the plenum volume and the flow introduced into the nasal cannula to provide a CO2 concentration to the nasal inserts of below approximately 0.5%.

7. The nasal cannula of claim 6 further comprising:

the one or more bleed ports located directly in line with one of the two nasal inserts for preferentially intercepting expired gas during an exhalation, the one or more bleed ports having a characteristic bleed port diameter called BPD, and the one or more bleed ports separated by a distance called L.

8. The nasal cannula of claim 6 further comprising:

the one or more bleed ports have a diameter between $3/8$ inches and $5/8$ inches.

9. The nasal cannula of claim 6 wherein:

the two nasal inserts terminate in compliant flanges at their distal ends to conform to the nare of a patient.

10. The nasal cannula of claim 9 wherein:

each of the two nasal inserts has a characteristic length;

the length of either the first or second nasal insert is sufficiently long to allow an insert to move in the nasal passage until the cross section area of the nare and the cross section area of the nasal insert are substantially the same, thereby forming a positive pressure seal between said nasal insert and said nare.

11. A nasal cannula, comprising:

a first nasal insert and a second nasal insert designed to be inserted and form a seal in the nares of a patient, the area disposed between the first nasal insert and the second nasal insert is not indented;

a first delivery tube and a second delivery tube each coupled to both the first nasal insert and the second nasal insert;

a coupler for coupling the nasal cannula to a source of respiration gas; and at least one bleed port positioned proximate a nasal insert having an opening flush with the exterior of the nasal cannula and an internal height less than ten times the thickness of the delivery tube at the location of the bleed port.

12. The nasal cannula as in claim 11, wherein the at least one bleed port communicates with the first and second delivery tubes and opens to atmospheric pressure.

13. The nasal cannula as in claim 11, wherein the at least one bleed port is substantially linearly aligned with one of the first nasal insert or second nasal insert.

14. The nasal cannula as in claim 11, wherein the at least one bleed port has a diameter between $3/8$ inches and $5/8$ inches.

15. The nasal cannula as in claim 11, wherein the at least one bleed port is located and sized to reduce the carbon dioxide content of inspired air to a value below between approximately 0.2% to 0.7% carbon dioxide for the air inhaled from and retained by the delivery tubes.

16. The nasal cannula as in claim 11, wherein the area between the first and second nasal inserts that is not indented increases the rigidity of the cannula.

17. The nasal cannula as in claim 11, wherein the first and second nasal inserts terminate in a compliant flange at their distal ends to conform to the nare of a patient.

18. The nasal cannula as in claim 17, wherein the nares of a patient will deform the shape of the first and second nasal inserts and their compliant flanges to form a seal between the nasal cannula and the nares of the patient.

19. The nasal cannula as in claim 11, wherein the length of either the first or second nasal insert are sufficiently long to allow an insert to move in the nasal passage until the cross section area of the nare of a patient and the cross section area of the nasal insert are substantially the same, thereby forming a positive pressure seal between said nasal insert and said nare.

20. The nasal cannula as in claim 11, wherein the coupler is y-shaped.

* * * * *